United States Patent [19]

Rochat et al.

[11] Patent Number: 4,760,004
[45] Date of Patent: Jul. 26, 1988

[54] THIOQUINACRIDONES AND ISOTHIOQUINACRIDONES, PREPARATION AND USE THEREOF

[75] Inventors: Alain C. Rochat, Fribourg, Switzerland; Edward E. Jaffe, Wilmington, Del.; Jin Mizuguchi, Marly, Switzerland

[73] Assignee: Ciba-Geigy Corporation, Ardsley, N.Y.

[21] Appl. No.: 119,525

[22] Filed: Nov. 12, 1987

Related U.S. Application Data

[63] Continuation-in-part of Ser. No. 929,299, Nov. 10, 1986, abandoned.

[51] Int. Cl.$^4$ .................. G03G 5/06; G03G 5/14; C07D 471/02
[52] U.S. Cl. ..................... 430/58; 430/59; 430/78; 430/130; 546/49; 546/56; 546/57; 8/662; 106/497; 136/263
[58] Field of Search ............... 430/58, 59, 76, 78, 430/130; 546/49, 56, 57; 8/662; 106/288 Q

[56] References Cited

U.S. PATENT DOCUMENTS

| | | | |
|---|---|---|---|
| 3,259,514 | 7/1966 | Graham | 546/56 X |
| 3,474,020 | 10/1969 | Tulagin et al. | 430/78 X |
| 3,667,943 | 6/1972 | Weinberger | 430/78 |
| 3,667,944 | 6/1972 | Weinberger | 430/78 |
| 3,667,945 | 6/1972 | Tulagin | 430/78 |
| 3,888,665 | 6/1975 | Wiedemann | 430/76 X |

FOREIGN PATENT DOCUMENTS 911206  11/1962  United Kingdom .................. 546/49

*Primary Examiner*—Roland E. Martin
*Attorney, Agent, or Firm*—Harry Falber

[57] ABSTRACT

Compounds of the formulae I, II and III

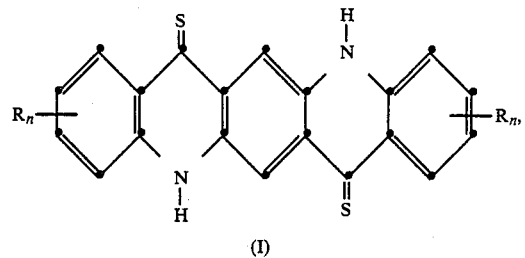

(I)

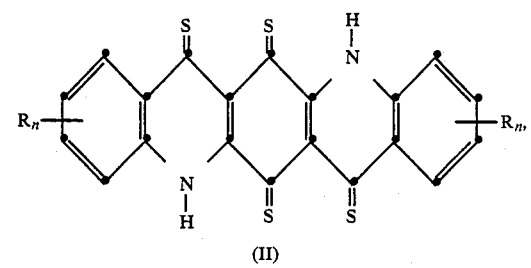

(II)

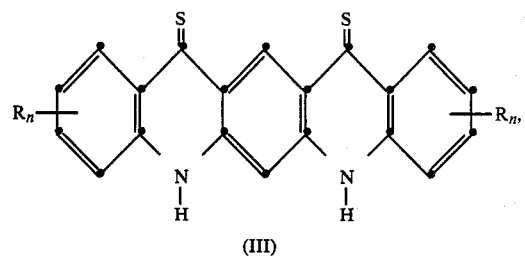

(III)

in which R is —F, —Cl, —Br, $C_1$–$C_{18}$alkoxy, and n is the number 0, 1, 2 or 3, are suitable in particular for use as photoconductive substances.

11 Claims, No Drawings

THIOQUINACRIDONES AND ISOTHIOQUINACRIDONES, PREPARATION AND USE THEREOF

CROSS-REFERENCE

This is a continuation-in-part of application Ser. No. 929,299 filed Nov. 10, 1986, now abandoned.

The invention relates to novel thioquinacridones and isothioquinacridones, to a process for their preparation and to their use as photoconductive substances and for colouring high molecular weight organic material.

Quinacridones have been described for a long time and are in particular useful pigments for colouring high molecular weight organic materials. Thioquinacridones, by contrast, have hitherto not been described.

The present invention accordingly provides compounds of the formula I, II or III

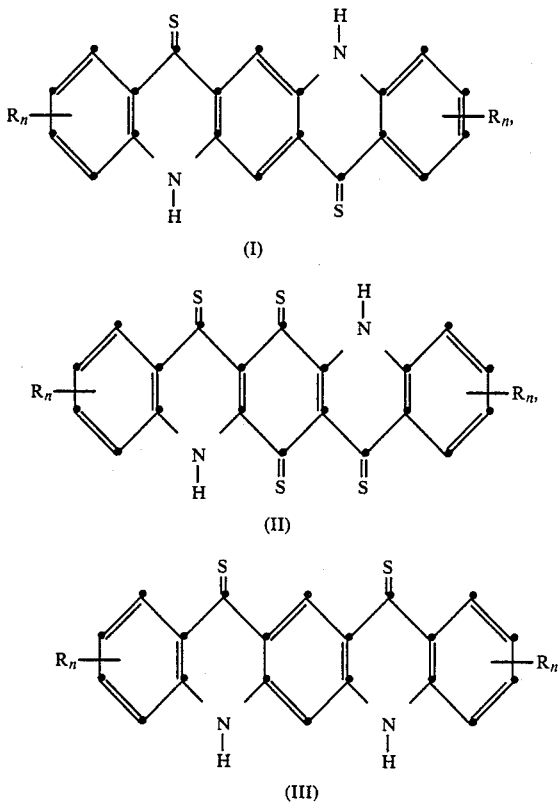

in which R is —F, —Cl, —Br, $C_1$–$C_{18}$alkyl or $C_1$–$C_3$alkoxy, and n is the number 0, 1, 2 or 3.

A $C_1$–$C_{18}$alkyl R can be branched or unbranched and preferably has 1–12, in particular 1–6, and particularly preferably 1–3, C atoms. Examples are methyl, ethyl, propyl, isopropyl, butyl, sec.-butyl, tert.-butyl, pentyl, isopentyl, tert.-pentyl, neopentyl, hexyl, neohexyl, octyl, 2-ethylhexyl, decyl, dodecyl and stearyl.

n is in particular the number 0 or 1.

Of particular interest are compounds of the formulae I and II in which R and n are as defined above.

Of very particular interest are compounds of the formula I in which n is the number 0 or 1 and R is —F, —Cl, —Br, —CH₃ or —OCH₃.

The compounds of the formulae I to III are obtained for example by heating a quinacridone, quinacridonequinone or isoquinacridone which conforms to one of the formulae I to III with S replaced by O, together with a thionating agent. Examples of suitable thionating agents are tetraphosphorus trisulfide ($P_4S_3$), tetraphosphorus heptasulfide ($P_4S_7$), tetraphosphorus decasulfide ($P_4S_{10}$) and also its pyridine complex $P_4S_{10} \times 4C_5H_5N$, furthermore dithiaphosphetanes and in particular 2,4-bis-(4'-methoxyphenyl)-1,3-dithia-2,4-diphosphetane-2,4-disulfide which is known as Lawesson's reagent. The latter and tetraphosphorus decasulfide are preferred. Further arylthionophosphine sulfides are also suitable and are described, for example, in the survey "Tetrahedron, Vol. 41, No. 22, pp. 5061–5087, in particular p. 5062, (1985), M. P. Cava and M. I. Levinson". The reaction is expediently carried out at temperatures between 50° and 250° C. with an excess of thionating agent, preferably between 80° and 160° C., and in an inert organic solvent. Suitable solvents are for example aromatic hydrocarbons, such as benzene, toluene, xylene or tetrahydronaphthalene, chlorinated aromatic hydrocarbons, such as chlorobenzene and o-dichlorobenzene, ethers, such as ethylene glycol dimethyl ether or diethyl ether, furthermore diethylene glycol dimethyl ether or diethyl ether, anisole, dioxane or diphenyl ether, or even nitriles, such as acetonitrile or benzonitrile, amides which are inert towards thionating agents, such as hexamethylphosphoramide, and also thioamides, for example dimethylthioformamide, dimethylthioacetamide or tetraethylsulfamide, or mixtures of the solvents mentioned.

The resulting thioquinacridones and isothioquinacridones of the formulae I to III can in general be isolated by filtration. Depending on the use, an aftertreatment is necessary in order to increase the chemical purity (for example recrystallization or sublimation) and/or in order to change the crystal shape (for example conditioning in an organic solvent). Suitable solvents for this purpose are for example as follows: benzenes which are substituted by halogen atoms, alkyl or nitro groups, such as xylenes, chlorobenzene, o-dichlorobenzene or nitrobenzene, and also pyridine bases, such as pyridine, picoline or quinoline, furthermore ketones, such as acetone, methyl ethyl ketone or cyclohexanone, ethers such as ethylene glycol monomethyl or monoethyl ether or tetrahydrofuran, amides, such as dimethylformamide, dimethylacetamide or N-methylpyrrolidone, alcohols, such as methanol or ethanol, dimethyl sulfoxide, sulfolane, acetonitrile, benzonitrile, methyl acetate and ethyl acetate. After this solvent treatment the compounds of formulae I to III are in some cases already present in the desired crystal shape, so that a further thermal aftertreatment of the type specified for example on page 7 can be dispensed with.

Depending on the nature of the compounds of the formulae I to III, these compounds can be used as photoconductive substances for electrophotographic photoreceptors or organic solar cells or as pigments.

Of particular interest are the compounds of the formulae I to III, in particular of the formula I, for use as photoconductive substances in electrophotographic photoreceptors. These photoreceptors consist of a conductive base and a photoconductor which is insulating in the dark but becomes conductive on exposure to light. The structure can consist of one or more layers. In the case of a single layer, at least one photoconductive substance is dispersed in at least one binder or is directly evaporated onto a conductive base. A photoconductor preferably consists of at least one charge-generating layer which contains one or more photoconductive substances, and at least one charge-transporting layer.

The present invention accordingly also provides an electrophotographic photoreceptor consisting of at least one conductive base, a photoconductive layer and a charge-transporting layer, at least one of these layers containing at least one compound of the formulae I to III.

The conductive base can be a metal plate or foil which is untreated or has been pretreated, for example by roughening, and for example consists of aluminum, zinc, magnesium, copper or an alloy of these metals. In the case of aluminium, the pretreatment can take the form of anodizing. Suitable bases are also aluminium-evaporated plastic films and also polymer films having a metallized surface.

The photoconductor contains at least one compound of the formulae I, II or III as photoconductive substances, and charge-transporting substances, such as hydrazones or pyrazolines dissolved in polymer binders. Such a structure, after prior static charge build-up and imagewise exposure, permits the production of a corresponding pattern of charged and discharged areas (latent image), which can be transformed by known reprographic methods into a visible image.

The exposure can be to light in the visible wavelength region. However, it is a particular advantage of the compounds of the formulae I to III that they are also capable of absorbing radiation in the near infrared region and that they even have photoconductive properties in this wave-length region. Of particular interest is the region 700-900 nm, in which the gallium arsenide laser operates.

The compounds of the formulae I to III have a high dark resistance, which helps to preserve the static potential in areas which are not exposed to light.

If the photoconductor consists of a single layer, this layer contains one or more compounds of the formula I to III, expediently in finely divided form, if desired together with charge-transporting substances, in an organic binder. The binder is expediently film-forming, insulating and adhesive. Depending on application, it is soluble in organic solvents or in basic mixtures of organic solvents which may contain water. Particularly suitable binders are based on polycondensation or polyaddition products, such as polyamides, polyurethanes, polyesters, epoxy resins, phenoxy resins, polyketones, polycarbonates, polyvinyl ketones, polystyrenes, polyvinylcarbazoles, polyacrylamides, polymethyl methacrylates, polyvinyl butyrates, polyvinyl chlorides and also copolymers, for example styrene/maleic anhydride copolymers or styrene/methacrylic acid/methacrylic acid ester copolymers.

If the photoconductor consists of a plurality of layers, double layers are of particular interest. In this case, the conductive base has applied to it first a photoconductive layer and on top thereof a second, charge-transporting layer. The layers can also be applied in the reverse order. One of the layers, preferably the charge-generating layer, contains at least one compound of the formula I to III. This compound can be dissolved or finely dispersed in an organic binder. Application to the conductive base is effected for example by applying a solution or dispersion of the binder/pigment mixture in an organic solvent and subsequently evaporating the solvent. However, the compound of the formulae I to III can also be vapour-deposited onto the conductive base.

The second layer contains one or more charge-transporting substances, preferably dissolved or dispersed in an organic binder. Suitable charge-transporting substances are the various aromatic, preferably nitrogen-containing, compounds, such as hydrazones or aromatic amines, which may contain alkylidene bridges or radicals. Examples are the substances described in German Offenlegungsschrift No. 3,447,685 on pages 57-65.

Although the compounds of the formulae I to III according to the invention do not have the minimal absorption of 750 nm which is required for laser recording, they are suitable for use as photoconductive substances for such a purpose. This has been made possible by finding a method which permits shifting this absorption to longer wavelengths to an extent which is decisive for electrophotography. This is surprising since the similar solvent treatment of quinacridones generally leads to a shift towards shorter wavelengths. The said shift is expediently obtained by exposing the photographic photoreceptor obtained as described above for 1-2 hours to a solvent vapour, for example acetone, tetrahydrofuran, dimethylformamide, methanol, acetonitrile, 1-acetoxy-2-ethoxyethane, dimethyl sulfoxide or ethyl acetate vapour.

The publication by K. Arishima et al., Appl. Phys. Letters 40 (3), p. 279 (1982), discloses this method for shifting the wavelength for certain phthalocyanines. The shift obtained is towards longer wavelengths and amounts to about 90 nm. The application of this method to materials which contain the novel compounds of the formulae I to III gives a shift towards longer wavelengths of around 70 and more nm. This solvent treatment brings about an increase in the photoconductivity by about 3 to 100 units.

The same spectral shift as well as similar values for the dark resistance and the photocurrent are also obtained with the pulverulent compounds of the formulae I to III; they are first ground, then treated with a solvent, for example ethyl acetate, and subsequently applied by means of a binder to a base.

The invention accordingly also provides the preparation of an electrophotographic photoreceptor, which comprises applying a compound of the formulae I to III to a conductive base by means of an organic binder or by vapour deposition in vacuo, treating the layer thus prepared with an organic solvent in liquid or gaseous form and subsequently building up a second layer which contains an aromatic, nitrogen-containing compound. Suitable (charge-transporting aromatic nitrogen-containing compounds are for example those of the abovementioned type.

To improve the physical properties of the layers, the photoconductive layer and the charge-transporting layer can also contain additives, such as levelling agents, surfactants or plasticizers.

The compounds according to the invention of the formulae I, II and III, but in particular of the formula I, can further also be used as pigments for colouring high molecular weight organic material.

Depending on the intended use, the compounds according to the invention can be converted into a more hiding or more transparent pigmentary form.

If a more hiding pigmentary form is desired, an expedient method is in general a thermal aftertreatment in water or in an organic solvent, if necessary under pressure. Use is preferably made of organic solvents, such as benzenes which are substituted by halogen atoms, alkyl or nitro groups, such as xylenes, chlorobenzene, o- dichlorobenzene or nitrobenzene, and also pyridine bases, such as pyridine, picolines or quinolines, furthermore as ketones, such as cyclohexanone, alcohols, such as isopropanol, butanols or pentanols, ethers, such as ethylene glycol monomethyl or monoethyl ether, amides, such as dimethylformamide or N-methylpyrrolidone, and also dimethyl sulfoxide or sulfolane. The aftertreatment can also be carried out in water, if necessary under pressure, in the presence of organic solvent and/or with the addition of surface-active substances.

The choice of solvent and of the temperature for such a thermal aftertreatment depends strongly on the solubility in this solvent of the compound to be treated, so that it is advisable to select the optimal aftertreatment conditions, such as choice of solvent, concentration and temperature, in advance for every compound which is suitable according to the invention.

High molecular weight organic materials which can be coloured or pigmented with the compounds according to the invention are for example cellulose ethers and esters, such as ethylcellulose, nitrocellulose, cellulose acetate or cellulose butyrate, natural resins or synthetic resins, such as polymerization resins or condensation resins, such as amino resins, in particular urea- and melamineformaldehyde resins, alkyd resins, phenolic resins, polycarbonates, polyolefins, polystyrene, polyvinyl chloride, polyamides, polyurethanes, polyesters, rubber, caseine, silicone and silicone resins, individually or in mixtures.

The high molecular weight organic compounds mentioned can be present individually or in mixtures as plastic materials, melts or in the form of spinning solutions, lacquers, paints or printing inks. Depending on the intended use, it is advantageous to use the compounds according to the invention as toners or in the form of formulations. Based on the high molecular weight organic material to be pigmented, the compounds according to the invention can be used for example in an amount of 0.1 to 30% by weight.

The high molecular weight organic substances are pigmented with the compounds according to the invention for example by admixing such a compound, if desired in the form of masterbatches, to these substrates by means of roll mills, mixing or milling apparatuses. The pigmented material is then brought into the desired final form by methods known per se, such as calendering, pressing, extruding, brushing, casting or injection moulding. It is frequently desirable, in the preparation of non-rigid mouldings or to reduce brittleness, to incorporate plasticizers into the high molecular weight compounds before moulding. The plasticizers used can be for example esters of phosphoric acid, phthalic acid or sebacic acid. The plasticizers can be incorporated into the polymers before or after incorporation of the compound according to the invention. It is further possible, if different colours are to be obtained, to add to the high molecular weight organic substances, in addition to the compounds according to the invention, also fillers and/or other colouring constituents, such as white, coloured or black pigments, in any desired amounts.

For the pigmenting of lacquers, paints and printing inks, the high molecular weight organic materials and the compounds according to the invention, if desired together with additives, such as fillers, other pigments, siccatives or plasticizers, are finely dispersed or dissolved in a common organic solvent or solvent mixture. This can be done by dispersing or dissolving the individual components separately or several of them together, and only then combining all components.

The colorations obtained, for example in plastics, fibres, paints or prints, are distinguished in general by moderate to good general properties, such as colour strength, dispersibility, overlacquering, migration, heat, light and weathering stability, and also gloss.

The examples below illustrate the invention:

EXAMPLE 1

Synthesis of quino[2,3-b]acridine-7,14-dithione (=dithioquinacridone)

7.95 g of crude, unsubstituted quinacridone are suspended in 175 ml of o-dichlorobenzene, and 12.4 g of Lawesson's reagent (=2,4-bis-(4-methoxyphenyl)-1,3-dithia-2,4-diphosphetane-2,4-disulfide) are added. The suspension obtained is heated under nitrogen to 143° C. and is maintained at that temperature for 3 hours. The reaction mixture is cooled down to 100° C., the resulting greenish blue compound is filtered off and washed in succession with warm o-dichlorobenzene, cold methanol and acetone. Drying at 100° C. in a vacuum oven leaves 8.93 g of a crude product which is purified by recrystallization in dimethylsulfoxide (=DMSO) as follows:

5.0 g of the dry crude product are suspended in 150 ml of pure DMSO while purging with argon, and the mixture is heated to 140° C. After the product has gone into solution, this solution is gradually cooled down to about 80° C., in the course of which the product begins to crystallize out. After about 1 hour at 80° C. the suspension is cooled down to about 70° C. and is maintained at that temperature for 15 hours. The crystallized product is then filtered off at 70° C. and washed very carefully with warm methanol and then with cold acetone. Drying at 100° C. leaves 3.90 g of a powder, which corresponds to a yield of 80.9% of theory (based on the quinacridone used), which has a melting point of above 300° C. and conforms to the following structure

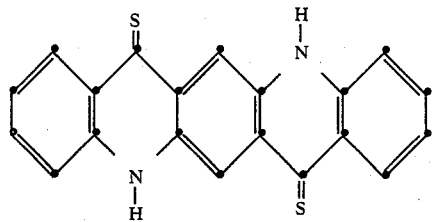

| Elemental analysis: | | | |
|---|---|---|---|
| Calculated | | Found | |
| C | 69.74% | C | 69.14% |
| H | 3.51% | H | 3.62% |
| N | 8.13% | N | 7.92% |
| S | 18.62% | S | 18.34% |

EXAMPLE 2

3.12 g (0.01 mol) of γ-quinacridone are suspended in 50 ml of hexamethylphosphoramide, and 4.85 g of Lawesson's reagent are added. The suspension obtained is heated to 130°–140° C. in the course of 30 minutes and is maintained with stirring at that temperature for a further 265 minutes. After cooling down to 80° C. the suspension is then poured into 300 ml of water, the resulting mixture is stirred for 30 minutes, and the resulting residue is filtered off, washed with water and then methanol and dried at 80° C. This gives 3.35 g (97.4% of theory) of a deep green product having a melting point of above 300° C. and containing, according to elemental analysis, 18.5% of sulfur (calculated amount 18.6%).

For analysis, the residue obtained above after pouring into water is suspended at room temperature in cold dimethylformamide, the resulting solution is clarified, and the resulting filtrate is diluted with methanol. The product thus precipitated is filtered off and dried to 80° C. The product conforms to the formula indicated in Example 1.

| Elemental analysis: | |
|---|---|
| Calculated | Found |
| C 69.74% | C 68.50% |
| H 3.51% | H 3.50% |
| N 8.13% | N 8.20% |
| S 18.62% | S 18.20% |

Extinction coefficient at 3 wavelengths of the visible region ($\epsilon$-value at $\lambda_{max}$) in dimethylformamide:
$\epsilon$-value: 13075 at $\lambda$647 nm 10172 at $\lambda$594 nm 4344 at $\lambda$552 nm.
X-ray diffraction diagrams (20° angle):
2 strong lines at 8.8 and 24.9;
4 medium lines at 12.7, 12.8, 17.7 and 27.1;
4 weak lines at 18.5, 19.5, 21.6 and 24.2.

EXAMPLE 3

1.56 g (0.005 mol) of quinacridone are suspended in 25 ml of dimethylthioformamide, 2.43 g (0.006 mol) of Lawesson's reagent are added, and the mixture is heated to 145° C. in the course of 45 minutes and is stirred at that temperature for 4½ hours. After cooling down to 60° C. the mixture is poured into 150 ml of methanol, and the resulting suspension is stirred at room temperature. The solids content is filtered off, washed with methanol until colourless and dried at 80° C. This gives 1.65 g (95.9% of theory) of a product which conforms to the formula indicated in Example 1 and, according to elemental analysis, contins 17.5% of sulfur (calculated: 18.6%).

EXAMPLE 4

1.56 g (0.005 mol) of quinacridone are suspended in 50 ml of xylene and 5 ml of hexamethylphosphoramide, 2.43 g (0.006 mol) of Lawesson's reagent are added, and the resulting mixture is heated to 130°-140° C. and is stirred at that temperature. After cooling down to 50° C. the reaction mixture is filtered to remove small amounts of unreacted material. The filtrate is poured into 200 ml of methanol, and the precipitated product is filtered off, washed with methanol and dried. This gives 1.42 g (82.6% of theory) of a deep green product which essentially has the same IR spectrum as the compound obtained in Example 2, but a different X-ray diffraction diagram:
three strong lines at 8.4, 12.8 and 26.0;
two strong lines at 12.2 and 27.5;
eight weak lines at 7.3, 10.2, 14.5, 16.7, 18.7, 22.2, 22.7 and 24.8.

This product is therefore another crystal modification of dithioquinacridone.

EXAMPLE 5

3.18 g (0.01 mol) of 2.9-dichloroquinacridone are suspended in 100 ml of hexamethylphosphoramide, 4.85 g (0.012 mol) of Lawesson's reagent are added, and the mixture is heated to 140°-145° C. in the course of 20 minutes. The mixture is stirred at that temperature for 4 hours, and is then cooled down to 60° C. and poured into 500 ml of water. The resulting suspension is stirred at room temperature for 30 minutes, and the product is filtered off and washed with water and then with methanol. This gives 4.5 g of crude product, which is recrystallized from 375 ml of dimethylformamide. This treatment gives 2.53 of a pure product which conforms to the following formula:

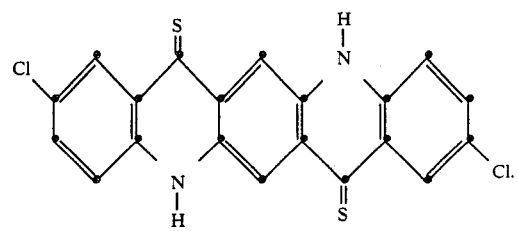

Elemental analysis for sulfur in %: Calculated: 15.5%. Found: 14.3%.

EXAMPLE 6

3.81 g (0.01 mol) of 4,11-dichloroquinacridone are suspended in 100 ml of o-dichlorobenzene, and 4.85 g (0.012 mol) of Lawesson's reagent are added under $N_2$; the resulting reaction mixture is heated to 145° C. and is stirred at that temperature for 4 hours. After cooling down to room temperature the suspension is poured into 200 ml of methanol, and the resulting product is filtered off, washed with methanol until colourless and dried at 80° C. This gives 4.12 g (100% of theory) of a product which, according to elemental analysis, contains 15.4% of sulfur (calculated: 15.5%) and has the following formula

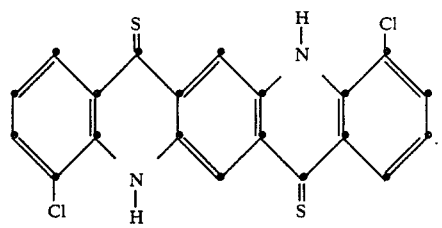

EXAMPLE 7

3.4 g (0.01 mol) of 2,9-dimethylquinacridone are suspended in 50 ml of hexamethylphosphoramide, 4.85 g (0.012 mol) of Lawesson's reagent are added, an the resulting mixture is heated to 135° C. in the course of 12 minutes and is stirred at that temperature for 5 hours. After cooling down to 60° C. the mixture is poured into 200 ml of methanol, and the resulting suspension is stirred at room temperature for 15 minutes, and the product is filtered off, washed with methanol and dried at 80° C. This gives 3.54 g (95.2% of theory) of a deep green product which, according to elemental analysis, contains 16.5% of sulfur (calculated: 17.2%) and has the following formula

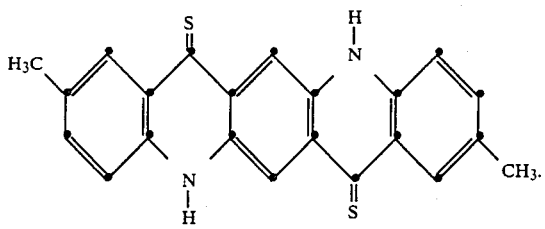

EXAMPLE 8

1.86 g (0.005 mol) of 2,9-dimethoxyquinacridone are suspended in 100 ml of o-dichlorobenzene, 2.43 g (0.006 mol) of Lawesson's reagent are added, and the resulting mixture is heated under nitrogen to 138°–142° C. and is stirred at that temperature for 4 hours.

The resulting reaction mixture is cooled down to room temperature and poured into 200 ml of methanol, and the resulting product is filtered off, washed with methanol until colourless and dried at 80° C. This gives 2.02 g (100% of theory) of a deep green product which after recrystallization in dimethylacetamide contains, according to elemental analysis, 15.3% of sulfur (calculated: 15.8) and conforms to the following structure

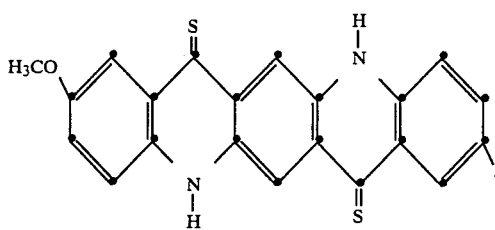

EXAMPLE 9

1.56 g (0.005 mol) of isoquinacridone are suspended in 50 ml of hexamethylphosphoramide, 2.43 g (0.006 mol) of Lawesson's reagent are added, and the mixture is heated to 140° C. and is stirred at that temperature for 4 hours. After cooling down to room temperature the reaction mixture is poured into 200 ml of methanol and stirred for 30 minutes. The resulting product is filtered off, washed with methanol and dried. This gives 1.81 g of a crude product.

For purification, 0.5 g of crude product is dissolved at 50°–60° C. in 100 ml of dimethylacetamide, the resulting solution is clarified, and 900 ml of methanol are added to the filtrate. The precipitated product is filtered off and dried at 80° C. This gives 0.35 g of a deep red product which, according to elemental analysis, contains 18.8% of sulfur (calculated: 18.6%), which has the following formula

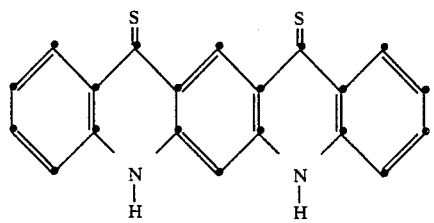

and which has molar extinction coefficients ($\epsilon$-values at $\lambda_{max}$) of 10021 (at $\lambda$563 nm) and 9914 (at $\lambda$541 nm) in dimethylformamide solution.

EXAMPLE 10

(thionation of quinacridonequinone):

6.85 g of quinacridonequinone (obtained by treating crude quinacridonequinone in boiling acetone) are suspended in a mixture of 140 ml of o-dichlorobenzene and 14 ml of hexamethylphosphoric acid triamide (=hexamethylphosphoramide). 19.8 g of Lawesson's reagent are added, and the resulting mixture is heated under nitrogen to 140° C. and is stirred at that temperature for 12 hours. The reaction mixture is cooled down to 60° C. and the resulting olive-green product is filtered off, washed with warm o-dichlorobenzene, then with cold dimethylformamide and finally with water and dried at 90° C. in an vacuum oven. This gives 6.72 g (82.7% of theory) of an olive-green product which, according to elemental analysis, contains 26.9% of sulfur (calculated: 31.54%) and which is recrystallized as follows: 4.0 g of the crude product are suspended in 100 ml of N-methyl-pyrrolidone (NMP) under nitrogen, and the resulting mixture is heated to 120° C. and stirred at that temperature for 6 hours. The resulting solid product is filtered off at that temperature, washed first with cold NMP, then with cold methanol and then with water and dried at 90° C. in a vacuum oven. This gives 2.29 g of a product which has a melting point of above 300° C. and a molecular weight of 406 (mass spectrometry) and conforms to the following structure

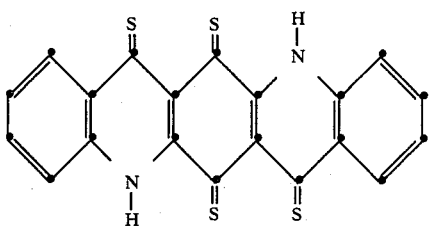

EXAMPLE 11

Into a four-neck, round bottom flask equipped with a stirrer, thermometer and reflux condenser were introduced 1.74 g (0.005 mol) of 2,9-difluoroquinacridone, 2.43 g (0.006 mol) of Lawesson's reagent and 50 ml of hexamethylphosphoramide. The mixture was stirred and heated to 140°–145° C. in 15 minutes. During the heat up period, several color changed occurred. At about 85° C. the yellowish red reaction mixture turned brownish red, at about 100° C. cherry red, at 110° C. violet, at 125° C. bluish violet, at about 130° C. deep blue and at about 145° C. the color turned deep green. The temperature was maintained at 140°–145° C. for 4.25 hours, the reaction mixture was cooled to 60° C. and drowned into 200 ml of stirred methanol. After stirring the resulting slurry for 20 minutes, the solid was filtered and washed thoroughly with methanol, until the filtrate was totally colorless. The dark greenish product was dried at 80° C. The yield was 1.76 g (92.6%) of 2,9-difluorodithioquinacridone. Percentage sulfur found 15.4; % sulfur calculated 16.8.

EXAMPLE 12

Using the same equipment as described in Example 11 the following materials were introduced: 3.48 g (0.01 mol) of 4,11-difluoroquinacridone, 4.86 g (0.012 mol) of Lawesson's reagent and 100 ml of o-dichlorobenzene. The mixture was stirred and heated to 140°–145° C. in 30 minutes. During the heating period, the color changed slowly from orange to brown, particularly after 100° C. was reached. The temperature was maintained at 140°–145° C. for 5 hours. During this period, the color of the precipitate changed to a dark, nearly black material. The reaction mixture was cooled to 60° C. and drowned into 200 ml of stirred methanol. After stirring the slurry for one hour, the solid was filtered and washed thoroughly with methanol until the filtrate was totally colorless. The greyish black solid was dried at 80° C. The yield was 3.74 g (98.4%) of 4,11-difluorodithioquinacridone. Percentage sulfur found 15.8; % sulfur calculated, 16.8.

EXAMPLE 13

0.5 g of the pigment obtained in Example 1 is dispersed in 15 g of a 7.5% solution of Lucite® 41 (a polymethyl methacrylate prepared by DuPont) in methyl ethyl ketone with 70 g of glass balls of 4–5 mm in diameter in a 50 ml capacity flask on a vibration ball mill (of the Vibratom® type from Siebtechnik of Mülheim/Ruhr) in the course of 16 hours. After removal of the glass balls the pigment dispersion is coated with a levelling rod onto an aluminium base in a wet film thickness of nominally 150 μm. Drying gives a layer having a thickness of about 15 μm and electrophotographic properties (E ½ at about 15 μJ/cm²).

EXAMPLE 14

0.3 g of the pigment of Example 1 is taken up in a mixture of 10 g of ethanol and methyl ethyl ketone (2:1 by volume), which contains 0.2 g of ethylcellulose. The suspension is then milled with glass balls for 5 hours and subsequently applied with a levelling rod to an aluminium plate (=photoconductive layer). This layer is dried at 50° C. in the course of 3 hours. The thickness of the layer is 6 μm. A second layer, which consists of a mixture of 0.6 g of a hydrazone of the formula

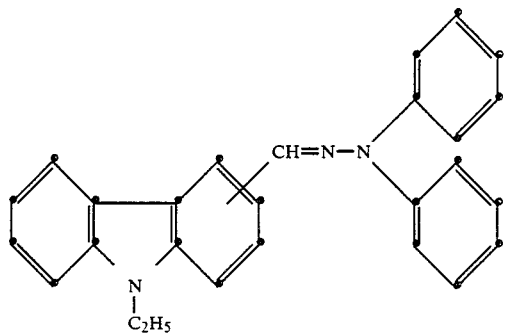

and 0.9 g of Lucite® 41 in 11 g of methyl ethyl ketone, is applied and dried at 50° C. in the course of 15 hours. The layer thickness is 10 to 15 μm. This photoreceptor has a sensitivity (E ½) of 6 μJ/cm², and the chargeability is 430 volt.

EXAMPLE 15

The pigment of Example 1 is vapour-deposited in a vacuum of $1.3 \times 10^{-6}$ bar onto an aluminium base at a rate of 5 Å/sec. The resulting layer thickness is 2000 to 3000 Å. This film is exposed at room temperature to acetone vapour for 1 hour. Subsequently a second layer of the same composition as in Example 14 is applied. The film has an absorption at 770 nm, which corresponds to a shift in the absorption by 70 nm (absorption of the corresponding film which has not been pretreated with acetone vapour: 700 nm).

EXAMPLE 16

The pigment of Example 1 is vapour-deposited as in Example 13, and the resulting film is exposed to dimethylformamide vapour for 1 hour. A second layer, the composition of which corresponds to that of Example 14, is applied on top. The film has an absorption at 770 nm.

EXAMPLE 17

0.4 g of the pigment of Example 1 is milled for 2 days in 10 ml of distilled water with 40 g of glass balls of 1 mm in diameter. The resulting product is filtered off and dried at 50° C. for 24 hours and then suspended in ethyl acetate for 1 hour, filtered off again and dried. The preparation of the monolayer is effected as in Example 13. The film has an absorption at 770 nm.

EXAMPLE 18

The pigment of Example 1, which is pretreated as in Example 17, is used to produce a double layer by the method of Example 14. The layer thus constructed has favourable electrophotographic properties.

EXAMPLE 19

0.5 g of the pigment of Example 10 is dispersed for 15 hours with glass balls in an AM-lacquer [mixture of an alkyd resin and a melamine resin in a solvent mixture of xylene and methyl glycol] as in Example 13. After removal of the glass balls the pigment dispersion is coated with a levelling rod onto an aluminium plate as in Example 13.

A second layer, the composition of which corresponds to that of Example 14, is applied on top. The photoreceptor has favourable electrophotographic properties.

We claim:
1. A compound of the formula I, II or III

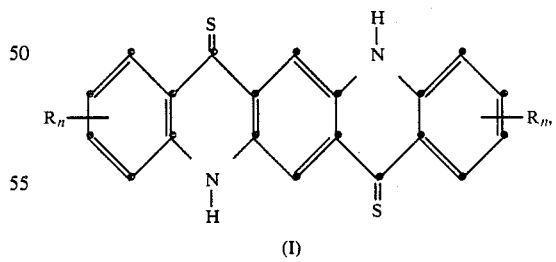

(I)

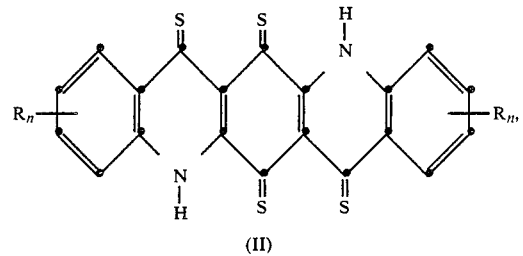

(II)

-continued

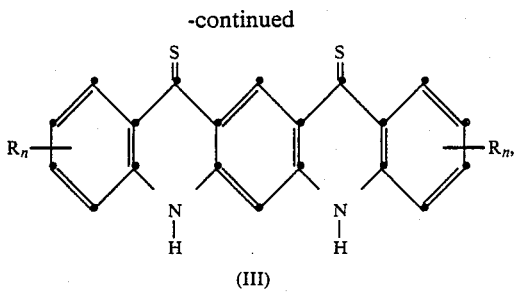

(III)

in which R is —F, —Cl, —Br, $C_1$-$C_{18}$alkyl or $C_1$-$C_3$alkoxy, and n is the number 0, 1, 2 or 3.

2. An electrophotographic photoreceptor consisting at least of a conductive base, a photoconductive layer and a charge-transporting layer, wherein at least one of these layers contains at least one compound of the formulae I to III according to claim 1.

3. An electrophotographic photoreceptor according to claim 1, wherein the photoconductive layer contains at least one compound according to claim 1.

4. A compound of the formula I or II according to claim 1, wherein R and n are as defined in claim 1.

5. A compound of the formula I according to claim 1, wherein R is —F, —Cl, —Br, —$CH_3$ or —$OCH_3$ and n is the number 0 or 1.

6. A process for preparing the compounds of the formulae I, II and III according to claim 1, which comprises heating a quinacridone, quinacridonequinone or isoquinacridone which conforms to one of the formulae I to III with S replaced by O, together with a thionating agent.

7. A process according to claim 4, wherein the thionating agent used is 2,4-bis-(4′-methoxyphenyl)-1,3-dithia-2,4-diphosphetane-2,4-disulfide or tetraphosphorus decasulfide.

8. A process according to claim 4, wherein the thionation reaction is carried out in an inert organic solvent.

9. Preparation of an electrophotographic photoreceptor, which comprises applying a compound according to claim 1 to a conductive base by means of an organic binder or by vapour deposition in vacuo, treating the layer thus prepared with an organic solvent in liquid or gaseous form and subsequently building up a second layer which contains an aromatic nitrogen-containing compound.

10. Preparation of an electrophotographic photoreceptor according to claim 9, wherein the solvent used is selected from the group consisting of acetone, tetrahydrofuran, dimethylformamide, methanol, dimethyl sulfoxide, ethyl acetate and acetonitrile.

11. A mass-coloured high molecular weight organic material containing a compound of the formula I according to claim 1.

* * * * *